United States Patent [19]
Thompson et al.

[11] Patent Number: 5,382,245
[45] Date of Patent: Jan. 17, 1995

[54] ABSORBENT ARTICLES, ESPECIALLY CATAMENIALS, HAVING IMPROVED FLUID DIRECTIONALITY

[75] Inventors: Hugh A. Thompson, Fairfield; Gerald A. Young; Thomas W. Osborn, III, both of Cincinnati; Charles W. Chappell, West Chester; Theresa L. Johnson, Cincinnati; John L. Hammons, Hamilton; Bruce W. Lavash, West Chester; James C. Horney, Cincinnati; Lee M. Hines, Wyoming, all of Ohio

[73] Assignee: The Procter & Gamble Company, Cincinnati, Ohio

[21] Appl. No.: 915,286

[22] Filed: Jul. 23, 1992

Related U.S. Application Data

[63] Continuation-in-part of Ser. No. 734,404, Jul. 23, 1991, abandoned.

[51] Int. Cl.[6] .................... A61F 13/15; A61F 13/20
[52] U.S. Cl. .................................. 604/367; 604/368; 604/378; 604/385.1
[58] Field of Search ............... 604/367, 368, 375, 378, 604/385.1, 365

[56] References Cited

U.S. PATENT DOCUMENTS

| | | | |
|---|---|---|---|
| 810,130 | 1/1906 | Green | 604/378 |
| 2,662,527 | 12/1953 | Jacks | 128/290 |
| 3,121,040 | 2/1964 | Shaw | 161/177 |
| 3,665,921 | 5/1972 | Stumpf | 604/378 X |
| 3,670,731 | 6/1972 | Harmon | 128/284 |
| 3,779,246 | 12/1973 | Mesek et al. | 604/378 X |
| 3,860,003 | 1/1975 | Buell | 128/287 |
| 4,054,709 | 10/1977 | Belitsin et al. | 428/224 |
| 4,179,259 | 12/1979 | Belitsin et al. | 425/464 |
| 4,256,111 | 3/1981 | Lassen | 128/284 |
| 4,286,005 | 8/1981 | Berger | 428/167 |
| 4,381,325 | 4/1983 | Masuda et al. | 428/91 |
| 4,411,660 | 10/1983 | Dawn et al. | 604/378 X |
| 4,578,070 | 3/1986 | Holtman | 604/378 |
| 4,623,329 | 11/1986 | Drobish et al. | 604/29 |
| 4,637,819 | 1/1987 | Ouellette et al. | 604/369 |
| 4,654,040 | 3/1987 | Luceri | 604/385 R |
| 4,662,876 | 5/1987 | Wiegner | 604/380 |
| 4,670,011 | 6/1987 | Mesek | 604/378 |
| 4,701,177 | 10/1987 | Ellis et al. | 604/385 A |
| 4,707,409 | 11/1987 | Phillips | 428/397 |
| 4,710,187 | 12/1987 | Boland et al. | 604/385.2 |
| 4,723,954 | 2/1988 | Pieniak | 604/384 |
| 4,747,846 | 5/1988 | Boland et al. | 604/385.2 |
| 4,781,710 | 11/1988 | Megison et al. | 604/378 |
| 4,798,603 | 1/1989 | Meyer et al. | 604/378 |
| 4,822,453 | 4/1989 | Dean et al. | 604/375 |
| 4,834,736 | 5/1989 | Boland et al. | 604/385.2 |
| 4,842,594 | 6/1989 | Ness | 604/378 X |
| 4,842,792 | 6/1989 | Bagrodia et al. | 264/130 |
| 4,865,596 | 9/1989 | Weisman et al. | 604/368 |
| 4,868,031 | 9/1989 | Modrak et al. | 428/198 |
| 4,923,454 | 5/1990 | Seymour et al. | 604/368 |
| 4,950,264 | 8/1990 | Osborn, III | 604/385.1 |
| 4,954,398 | 9/1990 | Bagrodia et al. | 428/400 |
| 4,973,325 | 11/1990 | Sherrod et al. | 604/384 |
| 4,988,344 | 1/1991 | Reising et al. | 604/378 X |
| 5,057,368 | 10/1991 | Largman et al. | 428/397 |
| 5,069,677 | 12/1991 | Sakurai et al. | 604/365 X |

FOREIGN PATENT DOCUMENTS

| | | | |
|---|---|---|---|
| 193309 | 9/1986 | European Pat. Off. | A41B 13/02 |
| 301874 | 2/1989 | European Pat. Off. | D01D 5/253 |
| 397110 | 8/1990 | European Pat. Off. | A61F 13/46 |
| 391814 | 10/1990 | European Pat. Off. | D01D 5/253 |
| 472992A1 | 3/1992 | European Pat. Off. | D04H 1/70 |
| 481322A1 | 4/1992 | European Pat. Off. | A61F 13/48 |
| WO92/07535 | 5/1992 | European Pat. Off. | A61F 13/46 |
| 483816A1 | 5/1992 | European Pat. Off. | D04H 1/44 |
| 493728A1 | 7/1992 | European Pat. Off. | D04H 1/42 |
| 955625 | 1/1950 | France . | |
| 54-151617 | 11/1979 | Japan . | |

Primary Examiner—Randall L. Green
Assistant Examiner—Elizabeth M. Burke
Attorney, Agent, or Firm—William Scott Andes; Kevin C. Johnson; E. Kelly Linman

[57] ABSTRACT

The present invention provides absorbent articles, especially sanitary napkins, containing a fluid transport layer. In-use, the transport layer directs menses to a storage layer, thereby minimizing product failure and staining of undergarments. The transport layer can protrude into, or through, a topsheet to provide very aggressive transport of vaginal discharges. Preferably, the transport layer is a layer of fibers having external capillary channels.

9 Claims, 8 Drawing Sheets

ABSORBENT ARTICLES, ESPECIALLY CATAMENIALS, HAVING IMPROVED FLUID DIRECTIONALITY

TECHNICAL FIELD

This application is a continuation-in-part of application Serial No. 07/734,404 filed Jul. 23, 1991 now abandoned.

The present invention relates to absorbent articles especially catamenial articles such as sanitary napkins. Such articles are especially adapted for absorbing various body fluids, especially menses, while providing comfort and fit to the wearer.

BACKGROUND OF THE INVENTION

A wide variety of structures for disposable absorbent articles to collect body fluids are known in the art. Commercial absorbent articles include diapers, adult incontinence products, catamenials and bandages. Disposable products of this type comprise some functional members for receiving, absorbing and retaining fluids. Generally, such absorbent articles contain a core of absorbent materials mainly comprising fibrous cellulose. Typically, such articles include a fluid-permeable topsheet, an absorbent core and a fluid-impermeable backsheet.

In the case of catamenial pads, women have come to expect a high level of performance in terms of comfort and fit, retention of fluid, and minimal staining. Above all, leakage of fluid from the pad onto undergarments is regarded as totally unacceptable.

Improving the performance of sanitary napkins continues to be a formidable undertaking, although a number of improvements have been made in both their materials and structures. However, eliminating leakage, particularly along the inside of the thighs, without compromising fit and comfort, has not met the desired needs of the consumer.

Leakage from sanitary napkins is generally attributed to a high concentration of fluid at the point where the menses exits the body and immediately contacts the surface of the napkin. At this point of deposit, the napkin's absorbent material quickly becomes supersaturated. The blood migrates radially from this point and leaks from the sides nearest the wearer's legs. This often results in the smearing of blood on the body and soiling of the undergarments. Attempts to eliminate leakage include: construction of a densified edge to hold the fluid back (U.S. Pat. No. 4,820,295, Chapas et al, issued Apr. 11, 1989); barrier sheets surrounding the article (U.S. Pat. No. 4,666,439, Williams et al, issued May 19, 1987); and "winged" side edges which wrap around the panties (U.S. Pat. No. 4,701,177, Ellis et al, issued Oct. 10, 1987, incorporated herein by reference).

Unfortunately, over-densifying sections of the sanitary napkins detracts from comfort, in-use. Some users are not attracted to the "winged" product, and others are not satisfied with the barrier product. However, since a large part of most absorbent articles remains relatively dry and not utilized, it has now been determined that providing a means to direct fluid from the point of deposit to the areas of the article not fully utilized will avoid supersaturation and considerably reduce or eliminate leakage.

Apart from undergarment soiling, the user of modern sanitary napkins, and the like, has come to expect that the surface of such articles will provide a cleaner, more sanitary and drier aspect than common cloth or nonwoven materials have historically provided. Thus, modern sanitary napkins, diapers and incontinence devices are typically provided with topsheets that are designed to move fluids rapidly through said topsheets and into an underlying absorbent core for storage. As can be envisaged, the more rapid and thorough this movement, the drier and cleaner the surface of the article.

Stated succinctly, the present invention not only provides the desired, directional movement of fluids noted above, which allows improved use of the overall absorbent capacity of the article and less side-leakage, but also provides means to draw fluids through the topsheet, thereby enhancing the desired dry, sanitary benefits, in-use.

Furthermore, the articles which employ the technology embodied in the present invention are more comfortable and better fitting than articles which rely, for example, on highly dense absorbent core regions to achieve fluid movement. Stated otherwise, the technology herein achieves the fluid directionality and handling characteristics available from dense, but uncomfortable, cores in a soft, pliable, low-density and comfortable pad.

SUMMARY OF THE INVENTION

The present invention pertains, in a preferred embodiment, to absorbent articles, preferably a sanitary napkin or pantiliner, but also including diapers, adult incontinence garments, bandages, and the like. The absorbent article has a longitudinal direction, a transverse direction, and a z-direction. The absorbent article includes a liquid-pervious topsheet and a liquid-impervious backsheet joined to said topsheet. An absorbent core is positioned between said topsheet and said backsheet. The core has an uppermost surface facing said topsheet and a lowermost surface facing said backsheet. A transport layer having a lower portion and an upper portion is positioned where the lower portion of said transport layer is below the uppermost surface of said core and is oriented substantially in the longitudinal direction. The upper portion of the transport layer extends at least to the uppermost surface of the absorbent core toward said topsheet and contains elements oriented substantially in the z-direction. Preferably the transport layer extends above the uppermost surface of the absorbent core.

In a preferred embodiment, the transport layer comprises fibers having external capillary channels. The capillary channel fibers are typically hydrophilic or preferably hydrophilized. In a highly preferred embodiment, the capillary channel fibers have a "C"-shaped cross-section with stabilizing legs depending therefrom.

Preferred structures of the foregoing types are wherein the capillary channel fibers are substantially curled.

Preferably the topsheet comprises an aperture permitting the transport layer to directly contact the wearer's skin.

In another preferred embodiment, the transport layer is gathered into a plurality of tufts. The tufts are oriented substantially in the z-direction and have an upper portion extending above the uppermost surface of the core and a lower portion extending below the uppermost surface of the core. The upper portion of the tufts may be cut in one embodiment of the present invention.

In another preferred embodiment, the present invention provides an absorbent article having a longitudinal direction, a transverse direction, and a z-direction. The absorbent article includes a liquid-pervious topsheet and a liquid-impervious backsheet joined to the topsheet. A primary absorbent core is positioned between the topsheet and the backsheet. The primary absorbent core has a first surface facing the body of the user and a second surface aligned opposite the first surface. A transport layer for facilitating movement of bodily fluids from the topsheet is positioned above the first surface of the primary absorbent core. The transport layer has a lower portion and an upper portion. The upper portion of its transport layer is oriented substantially in the z-direction toward the topsheet. The lower portion of the transport layer is oriented substantially in the longitudinal direction. A secondary absorbent structure substantially surrounds the upper portion of the transport layer.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein;

DETAILED DESCRIPTION OF THE INVENTION

1. General Description of the Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinence pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
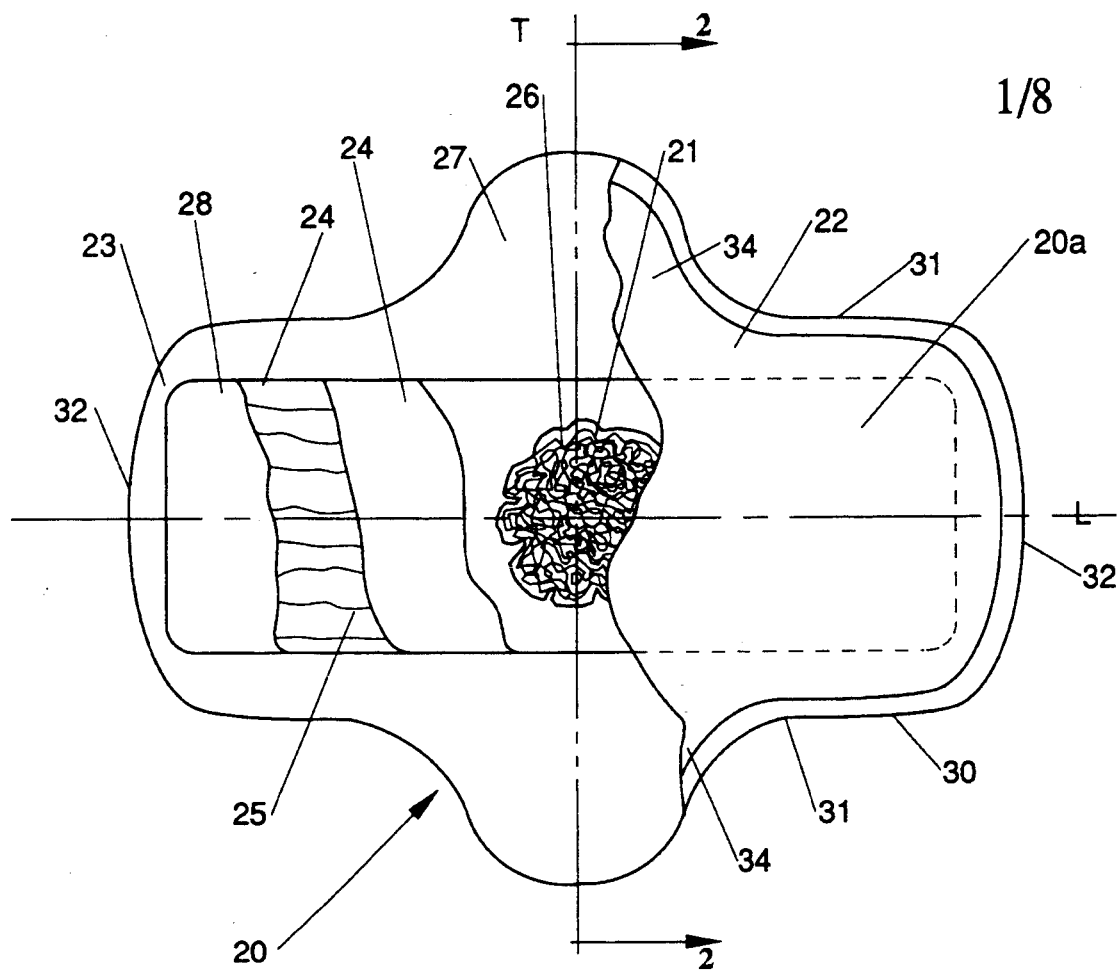
FIG. 1 is a top plan view of a preferred sanitary napkin of the present invention with portions cut-away to more clearly show the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer 20a, oriented towards the viewer. As shown in FIG. 1, the sanitary napkin 20 preferably comprises a liquid-pervious topsheet 22, a liquid-impervious backsheet 23 joined with the topsheet 22, an absorbent core 24 positioned between the topsheet 22 and the backsheet 23, and a transport layer 21 positioned below the topsheet 22. Preferably the transport layer 21 comprises fibers 25 having external capillary channels which are arranged in a tufted bundle (or "bun") 26.

The sanitary napkin 20 can also be provided with one or more addition layers or components. These include an acquisition layer (or the "secondary topsheet") 27 positioned generally between the topsheet 22 and the absorbent core 24. The sanitary napkin 20 also includes a non-woven layer 28 positioned between the absorbent core 24 and the backsheet 23. The nonwoven layer 28 serves to keep the material of the core 24 from tearing (when the core is comprised of a cross-linked cellulose fibers) and the layers of the sanitary napkin 20 are stitched.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes optional side flaps or "wings" 34 that are folded around the crotch portion of the wearer's panties. The side flaps 34 can serve a number of purposes, including, but not limited to, protecting the wearer's panties from soiling and keeping the sanitary napkin secured to the wearer's panties.

Figure 2:
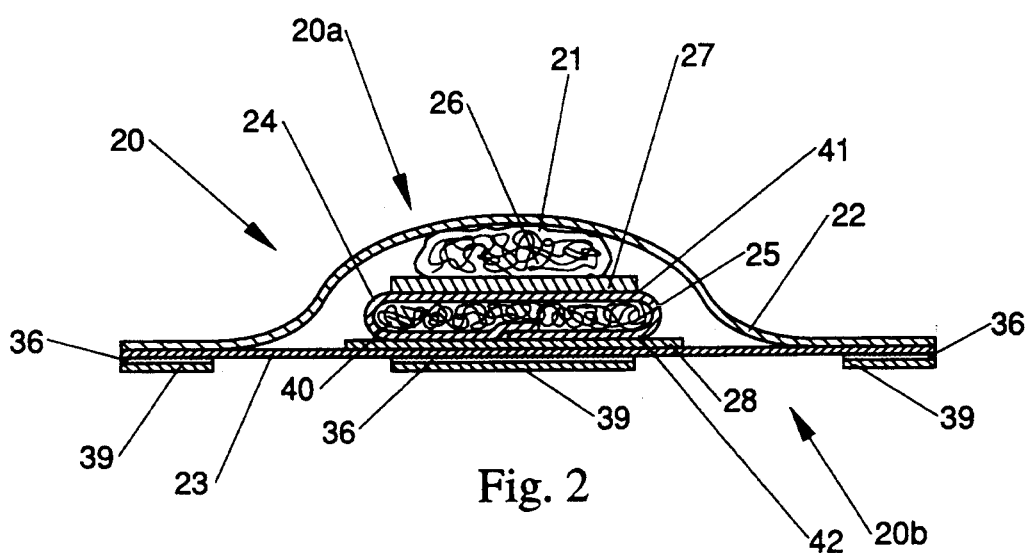
FIG. 2 is a cross-sectional view of the sanitary napkin of Figure taken along line 2—2.
Figure 3:
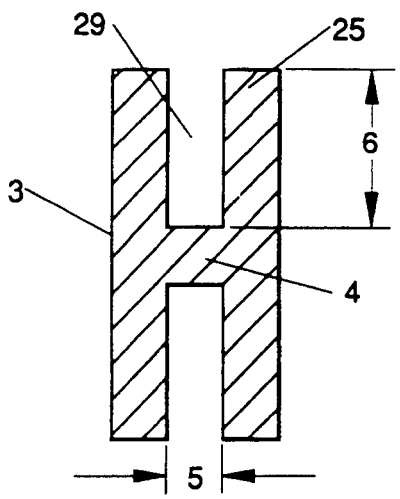
FIG. 3 is a cross-sectional view of a symmetrical "H" shaped capillary channel fiber with a planar base (4), width between walls (5), and depth-of-walls (6)

FIG. 2 is a cross-sectional view of the sanitary napkin 20 taken along section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 39 cover the adhesive fastening means 36 to keep the adhesive from sticking to a surface other than the crotch portion of the undergarment prior to use.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. The sanitary napkin 20 also has a "z" direction or axis, which is the direction proceeding down through the topsheet 22, thence into the transport layer 21, and thence into whatever fluid storage core 24 that may be provided. The objective is to provide a gradient of capillary suction between the topsheet 22 and underlying layer or layers of the articles herein, such that fluid is drawn in the "z" direction and away from the surface of the article into its ultimate storage layer. Empirically, capillary suction is related to the contact angle of the material and inversely related to the size of the openings—i.e., in the typical case, the openings in the topsheet will be larger than the intra-fiber capillary channels, which, in turn, will be larger than the intra-fiber capillary channels in a fibrous storage core. The surface hydrophilicity of the components of each layer can theoretically affect the capillary suction gradient.

Simply stated, the capillary channel fibers used herein promote passage of fluids in the "z" direction of absorbent articles. Moreover, by employing a layer of capillary channel fibers whose fibers are positioned to lie substantially parallel to the longitudinal direction, fluid flow in the longitudinal direction is also promoted, which enhances the overall useful absorbency of the article. However, by thus positioning the capillary channel fibers, fluid flow in the transverse direction is controlled, thereby minimizing, or even entirely avoiding, leakage of fluid around the lateral edges of the article. Thus, unlike absorbent articles of the prior art which move fluids in an undirected manner in the x, y and z directions by means of fibrous batts which comprise inter-fiber capillary voids, the interfiber capillary channels of the fibers herein can be used to provide desirable fluid directionality. Moreover, since the capillaries of the fibrous layer of the present invention reside in the fibers, themselves, rather than in inter-fiber spacings, capillarity is not lost when fiber-fiber spacings become displaced. In addition, the capillary channel fiber layer of the present invention provides its fluid drawing and directing functions even when the layer is soft, fluffy, low density and comfortable to the wearer, in contrast to compact, dense and relatively stiff batt materials which function by inter-fiber capillary action. Thus, it will be appreciated that the absorbent articles of this invention function in a substantially different way, using substantially different materials to provide substantially different benefits than the various absorbent structures disclosed in the art which do not employ a transport layer preferably comprised of fibers having intrafiber capillary channels to promote the passage of bodily fluids in the z-direction.

The individual components of the sanitary napkin will now be described at in greater detail.

2. Individual Components of the Sanitary Napkin

A. The Topsheet

The topsheet 22 is compliant, soft feeling, and non-irritating to the wearer's skin. Further, the topsheet 22 is liquid pervious permitting liquids (e.g., menses and/or urine) to readily penetrate through its thickness. A suitable topsheet 22 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

A preferred topsheet 22 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 4,629,643, issued to Curro et al. on Dec. 16, 1986; and U.S. Pat. No. 5,006,394, issued to Baird on Apr. 9, 1991. Each of these patents are incorporated herein by reference. The preferred topsheet 22 for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet 22 is hydrophilic so as to help liquid to transfer through the topsheet 22 faster than if the body surface was not hydrophilic. This will diminish the likelihood that menstrual fluid will flow off the topsheet 22 rather than flowing into and being absorbed by the absorbent core 24. In a preferred embodiment, surfactant is incorporated into the polymeric materials of the formed film topsheet 22 such as is described in U.S. patent application Ser. No. 07/794,745, entitled "Absorbent Article Having A Nonwoven and Apertured Film Coversheet" filed on Nov. 19, 1991 by Aziz et al abandoned. Alternatively, the body surface of the topsheet 22 can be made hydrophilic by treating it with a surfactant such as is described in U.S. Pat. No. 4,950,264 issued to Osborn on Aug. 21, 1991 and U.S. Pat. No. 5,009,653, issued to Osborn on Apr. 23, 1991 both of which are incorporated herein by reference.

B. The Absorbent Core

Figure 11:
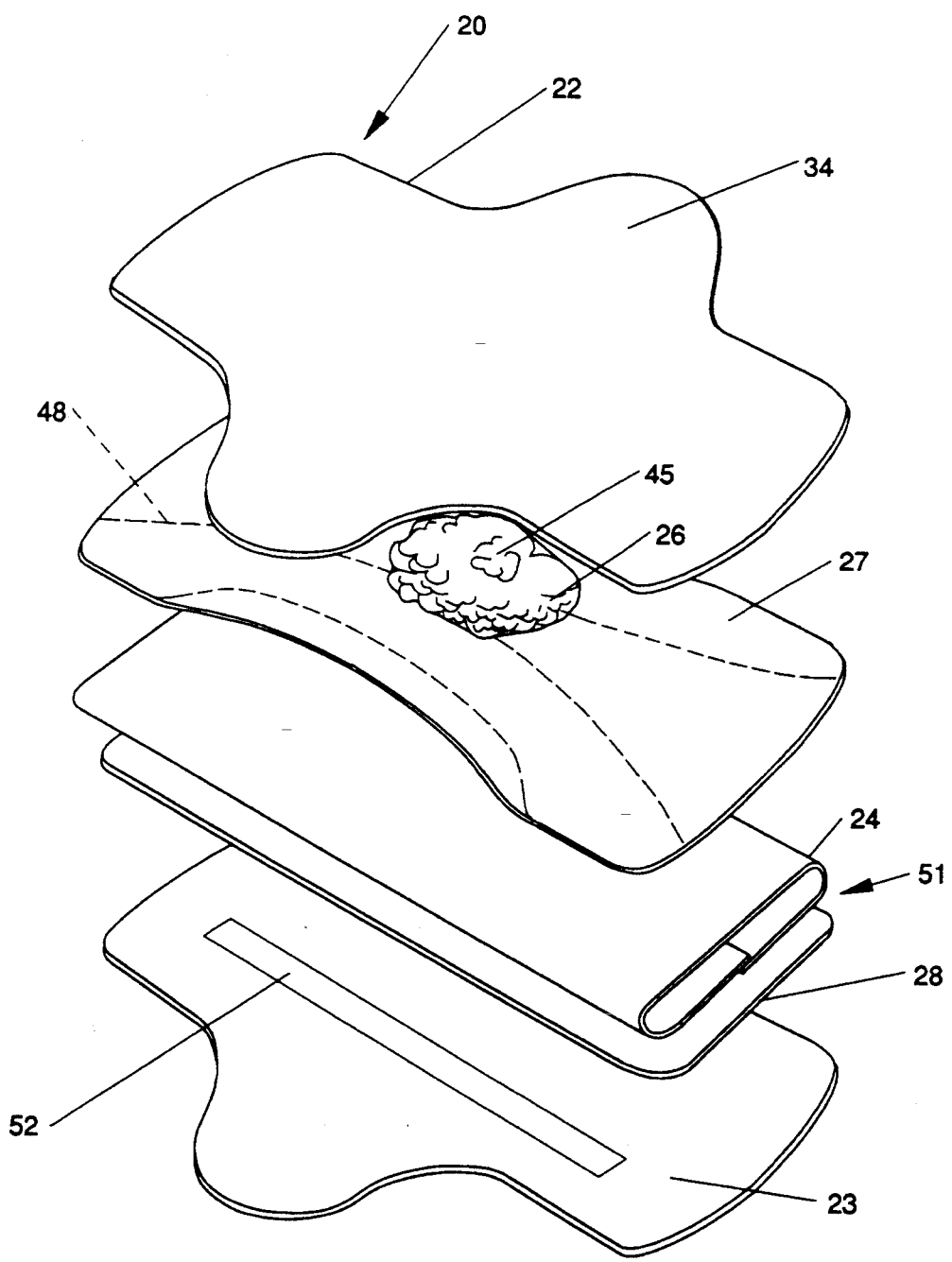
FIG. 11 is an exploded perspective view showing the assembly of one version of the sanitary napkin shown in FIG. 1.

The absorbent core 24 may be any absorbent means which is capable of absorbing or retaining liquids (e.g., menses and/or urine). As shown in FIGS. 2 and 11, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles, such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264, issued to Osborn on Aug. 21, 1990; U.S. Pat. No. 4,610,678, issued to Weisman et al. on Sep. 9, 1986; U.S. Pat. No. 4,834,735, issued to Alemany et al. on May 30, 1989; U.S. Pat. No. 5,009,653, issued to Osborne on Apr. 23, 1991; and European Patent Application No. 0 198 683, The Procter & Gamble Company, published Oct. 22, 1986 in the name of Duenk et al. Each of these patents are incorporated herein by reference.

A preferred embodiment of the absorbent core 24 comprises the laminate structure shown in FIGS. 2 and 11. The laminate is comprised of a layer of superabsorbent polymeric (or absorbent gelling material) and one or more sheets or webs of cross-linked cellulosic fibers. Suitable cross-linked cellulosic fibers for the absorbent core 24 are described in U.S. Pat. No. 4,888,093 issued to Cook et al. on Dec. 19, 1989; U.S. Pat. No. 4,822,543, issued to Dean et al. on Apr. 18, 1989; U.S. Pat. No. 4,889,595, issued to Schoggen et al. on Dec. 26, 1989; and U.S. Pat. No. 4,898,642, issued to Moore et al. on Feb. 6, 1990; U.S. Pat. No. 4,935,022, issued Jun. 19, 1990 to Lash et al.; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991, all of which are incorporated herein by reference.

The cross-linked cellulosic fibers in the embodiment shown in FIGS. 2 and 11 comprises a single sheet that wraps the layers of particles of absorbent gelling material 40. The sheet is wrapped so that it appears as having a "c" configuration when viewed from the end. The wrapped sheet forms an upper layer 41 and a lower layer 42. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemical stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as cross-linking agents. In addition, polycarboxylic acids can be used as cross-linking agents. It will be appreciated that other means for preparing other cross-linked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types. Once in hand, the curled cellulosic fibers are refined to provide the fibers used to prepare the preferred absorbent cores used in the practice of this invention.

C. Backsheet

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more cloth-like appearance. Further, the backsheet 23 may permit vapors to escape from the absorbent core 24 (i.e., breathable) while still preventing exudates from passing through the backsheet 23.

D. The Capillary Channel Fiber Bun

The sanitary napkin 20 preferably has a tufted bundle (or "bun") 26 of capillary channel fibers 25 that are positioned generally between the backsheet 23 and the topsheet 22. Capillary channel fibers 25 are fibers having channel s formed therein, preferably, on their exterior surfaces. FIGS. 3 to 7c show examples of some types of capillary channel fibers 25. Suitable capillary channel fibers are described below, and in the following Patent Applications which were filed on Jul. 23, 1991: U.S. patent applications Ser. No. 07/734,404 filed in the names of Thompson et al. (now abandoned); U.S. patent application Ser. No. 07/734,392 filed in the names of Thompson et al. (now abandoned); and, U.S. patent application Ser. No. 07/734,405 filed in the names of Buenger et al pending. These patent applications may be referred to collectively as the "capillary channel fiber" patent applications. Suitable capillary channel fibers are also described in EPO Patent Application 0 391 814 published Oct. 10, 1990.

While a variety of capillary channel fibers can be used herein, the following description discusses some preferred characteristics of the capillary channel fiber 25 that are incorporated into the absorbent articles of this invention.

(1). Fiber Morphology

The capillary channel fibers 25, as noted above, have capillary channels 29 on their outer surfaces. While the capillary channel fibers can also have a hollow central core which would provide some additional capillarity, it is preferred that such hollow core fibers not be employed. In general, providing capillary channel fibers with a central hollow core would require the fibers to be somewhat stiffer than desired in order that the core not collapse under pressure. A central core running through a capillary channel fiber would not be expected to quickly pick up fluids, since the fluids would have to find their way to the end of a fiber before proceeding into the core itself. Moreover, a hollow core capillary channel fiber could not release its load of fluid into an absorbent reservoir core without having appropriate contact between the ends of the hollow core fiber and the reservoir core material.

The capillary channel fibers 25 are preferably bent or, most preferably, are in a curled configuration (that is, they are nonlinear). Most preferably, the capillary channel fibers 25 are "substantially curled" (or otherwise gathered). This provides the capillary channel fibers with a higher loft and increased resilience for a given number of fibers. By increasing the loft of the individual fibers, the overall loft of pads made therefrom is thicker and softer. This allows for the formation of low density, high loft pads which, assuming that the individual fibers themselves are not too thick or stiff are extremely comfortable, yet effective for transporting fluids.

However, the preferred nonlinear capillary channel fibers herein should not be "kinked". Kinking a capillary channel fiber can cause points of constriction of the capillary channels at each kinking site. This, of course, would interfere with fluid flow dynamics along the capillary channel.

Figure 8:
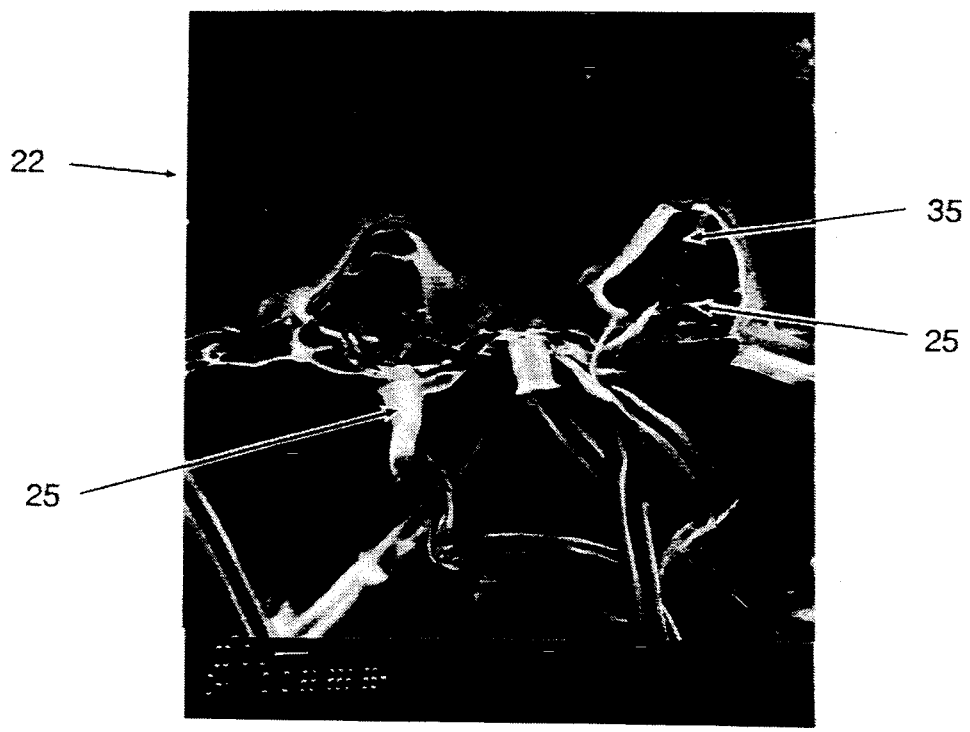
FIG. 8 is a photomicrograph sectional view taken of a sanitary napkin which shows the close contact between a formed film topsheet and an underlying layer of capillary channel fibers and the protrusion of capillary channel fibers into the pores of the topsheet.

In addition, there is another substantial advantage to employing nonlinear capillary channel fibers. As indicated in FIG. 8, it may be preferred that small portions, of the capillary channel fibers 25 actually protrude into at least some of the topsheet 22 orifices 35 of the articles herein. These protrusions are easier to effect when a capillary channel pad is prepared using curled capillary channel fibers. There is a greater likelihood that a number of ends and/or curls in the capillary channel fibers will find their way into the orifices of the topsheet material than if substantially linear capillary channels were to be employed. The capillary channel fibers 25 may be curled in a number of ways, including but not limited to: (1) selectively heat quenching the fibers as they come from their forming die by heating one side of the fibers a bit more than the other side (or, conversely, by cooling one side more quickly than the other); (2) fibers made from synthetic polymers such as polyesters can be curled by stretching, followed by relaxation, or by passing the fiber under tension around a sharp edge, followed by relaxation; or (3) by immersion in methanol. In a preferred mode, the fibers are substantially helical. Whatever means are used to crimp or otherwise curl the capillary channel fibers, they can, if desired, then be carded to form an assembly of fibers.

The preferred amplitude of the curls is in the range of about 0.1 mm to about 5 mm, and, typically, the frequency of the curls is from about 1 per inch of fiber to about 10 per inch of fiber. Fibers with amplitudes of about 0.5 mm and a frequency of about 6 crimps per inch exhibit good softness even in the higher denier ranged fibers having large capillary channels.

The capillary channel fibers 25 are intended to promote passage of liquids in the "z" direction of absorbent articles. The "z" direction, as shown in FIG. 2, is the direction proceeding down through the topsheet 22, then into the capillary channel fibers 25, and thence into whatever fluid storage core 24 may be provided.

The objective is to provide a gradient of capillary suction between the topsheet 22 and underlying layer or layers of the articles herein, such that the liquid is drawn in the "z" direction and away from the surface of the article and into its ultimate storage layer. Empirically, capillary suction is related to the contact angle of the material and inversely related to the size of the openings, i.e., in a typical case, the openings and the topsheet will be larger than the intra-fiber capillary channels, which, in turn, will be larger than the inter-fiber capillary openings in a fibrous storage core. The surface hydrophilicity of the components of each layer can also theoretically effect the capillary section gradient.

The capillary channel fibers 25 in at least the upper portion 45 of the tuft 26 are preferably oriented generally in the z-direction. Further, by providing some underlying capillary channel fibers that lie substantially parallel to the longitudinal direction, fluid flow in the longitudinal direction is also promoted, which enhances the overall useful absorbency of the article. Further, by orienting the capillary channel fibers of the lower portion 46 of the tuft 26 in the longitudinal direction, fluid flow in the transverse direction is controlled, thereby minimizing, or even entirely avoiding, leakage of fluid from the longitudinal side edges 31 of the article.

Thus, unlike absorbent articles of the prior art which utilize fibrous batts which comprise inter-fiber capillary voids and move liquids in an undirected manner and the x, y and z directions, the intrafiber capillary channels 29 of the capillary channel fibers 25 can be used to provide desirable fluid directionality. In addition, since the capillaries of the fibrous layer of the present invention reside in the fibers 25 themselves, rather than in the inter-fiber spacings, capillarity is not lost when fiber-fiber spacings become displaced.

In addition, the capillary channel fiber bun 26 of the present invention provides its liquid drawing and directing functions even when the bun 26 is soft fluffy and comfortable to the wearer, in contrast to compact, dense and relatively stiff batt materials which function by inter-fiber capillary action.

The tuft 26 of capillary channel fibers 25 forms a hump which is capable of fitting in the space between the wearer's labia. This allows the sanitary napkin to intercept body exudates readily when they leave the wearer's body. The hump is useful in placing the capillary channel fibers in the bun 26 in close proximity to the wearer's body. This is particularly true for the capillary channel fibers located in the upper portion of the bun 26. These fibers are preferably oriented in the z-direction. This allows the capillary channel fibers to draw liquids away from the wearer's body. The fit in the space between the wearer's labia is enhanced when the hump is formed from materials, such as capillary channel fibers, which are resilient. Preferably the materials forming the hump are both resilient when wet and dry. The resiliency allows the hump to adapt to the space between the wearer's labia more readily when the wearer moves about.

(2). Fiber Structure and Surface Properties

The capillary channel fibers 25 used herein can be prepared from any convenient polymer which is non-swelling when wet. Polymers such as polyethylene, polypropylene, polyesters (preferred), and the like, are useful herein, so long as they are spinnable such that they can be formed with external capillary channels, as noted hereinabove. Conveniently, the polymers are melt-extrudable. Typically, the capillary channel fibers herein will be prepared from a synthetic polyethylene terephthalate polymer melt having an inherent viscosity ("IV") of from about 0.6 to about 0.9. (IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9, since this would allow the walls of the capillary channels to be thinner, yet sufficiently strong to avoid collapse under in-use pressure.

The capillary channel fibers 25 preferably have a denier of about 10 to about 22. However, it is to be understood that the denier of the fibers used is within the discretion of the formulator, and the denier per fiber can easily be in the range of about 25 to about 35.

The depth:width ratio of the capillary channels herein is preferably about 2.0, but processing restrictions, as noted above, as well as for economic reasons, a depth:width ratio of about 1.3 is typically employed. Typical and readily producible capillary channel fibers which are quite satisfactory for use herein thus have a depth-of-walls of about 48 microns and a width-between-walls of about 37 microns. The walls, themselves, are typically about 3-15 microns thick. Although variations in these dimensions are acceptable, capillary channel fibers prepared from polyester and having these characteristics are quite effective for their intended purpose. Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

Figure 4:
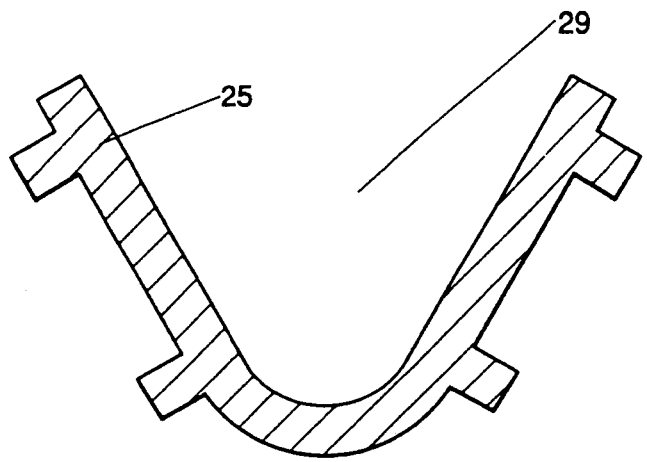
FIG. 4 is a cross-sectional view of a "C" shaped capillary channel fiber having stabilizing legs depending therefrom.
Figure 5:
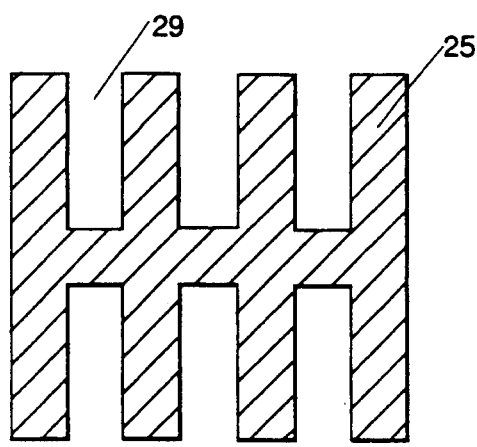
FIG. 5 is a cross-sectional view of a multiple "H"-shaped capillary fiber.
Figure 6:
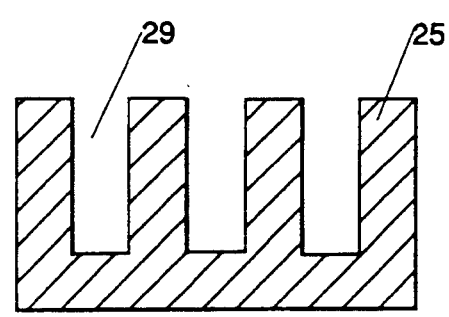
FIG. 6 is a cross-sectional view of a multiple "U"-shaped capillary channel fiber.
Figures 7A, 7B, 7C:
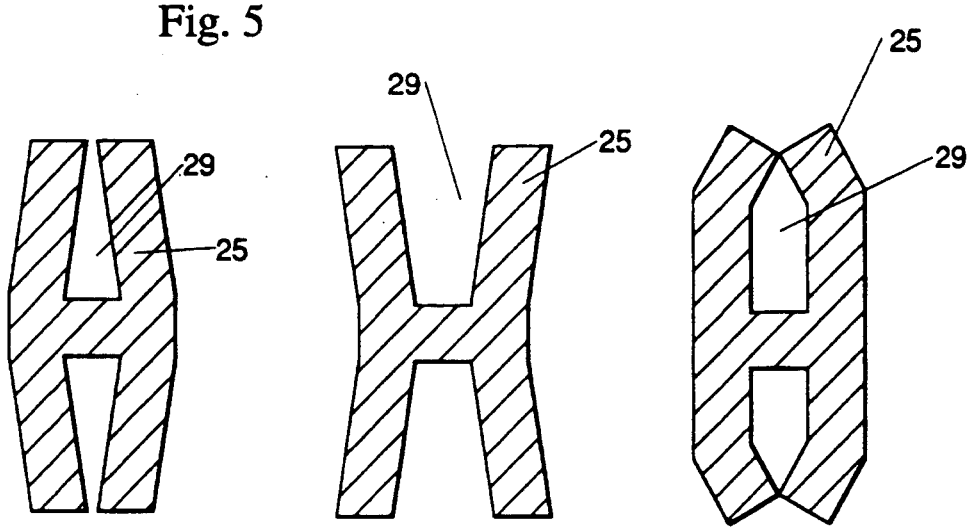
FIG. 7A is a cross-sectional view of an H-shaped capillary channel fiber in a partially collapsed state. (While not optimal, such fibers can be used herein)
FIG. 7B is a cross-sectional view of an expanded capillary channel fiber.
FIG. 7C is a cross-sectional view of a wholly collapsed capillary channel fiber; (Such fibers are not used herein)

The capillary channels 29 can be of various shapes. Certain shapes can offer particular advantages in particular product applications. For example, "U"-shaped, "H"-shaped, "C"-shaped with stabilizing legs depending therefrom and "V"-shaped capillary channels 25 may be used. The "C"-shaped fibers with stabilizing legs depending therefrom of FIG. 4 are one preferred shape. Furthermore, the basic shapes may be repeated (see Figures), or even branched, to produce fibers containing multiple channels, but it will be appreciated that when more than about three repeating shapes are used, some additional stiffness may be noted in the fibers. The multiple "U" fibers of FIG. 6 offer the additional advantages of having additional capillarity due to face-to-face contact and being easily curled.

The manufacturer of capillary channel fibers 25 of the type employed herein is described in EPO Application 391,814 and in co-pending U.S. Continuation-In-Part Application entitled "Fibers Capable of Spontaneously Transporting Fluids", Ser. No. 07/736,267, filed Jul. 23, 1991, Inventors Phillips, Jones et al., Eastman Chemical Company; U.S. Pat. No. 5,268,229 entitled "Spinneret Orifices and Filament Cross-Sections with Stabilizing Legs Therefrom", issued Dec. 7, 1993 to Inventors Phillips, et al.; and in U.S. Patent application entitled "Open Capillary Channel Structures, Improved Process for Making Capillary Channel Structures, and Extrusion Die for Use Therein", Ser. No. 07/482,446, filed Feb. 20, 1990, inventors Thompson and Krautter now abandoned.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic.

The surface treatment of polymeric fibers involves processes which are well-known in the extensive fiber literature. In general, such processes involve treating the surface of the fibers with a "hydrophilizing agent", especially a surfactant. (Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactants useful in such processes include various nonionic and anionic detersive surfactants of the general type known in the laundry literature. Hydrophilizing agents include wetting agents such as polyethylene glycol monolaurates (e.g., PEGOSPERSE 200 ML, a polyethylene glycol 200 monolaurate available from Lonza, Inc., Williamsport, Pa., USA), and ethoxylated oleyl alcohols (e.g., VOLPO-3, available from Croda, Inc., New York, N.Y., USA). Other types of hydrophilizing agents and techniques can also be used, including those well known to those skilled in the fiber and textile arts for increasing wicking performance, improving soil release properties, etc. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

(3). Arrangement of the Capillary Channel Fibers into Fibrous Batts

In general, the capillary channel fibers 25 will be laid down into a bundle of such fibers for use in the absorbent article. In a preferred embodiment, the capillary channel fibers 25 are laid down in a batt and gathered into a tuft or bun 26.

For use in disposable absorbent articles, such batts will typically have from about 0.003 g to about 0.016 g of fiber per 1 $cm^2$ surface area, and will have from about 0.003 g to about 0.03 g capillary channel fiber per 1 $cm^3$ volume (measured in the uncompressed state). The amounts of fiber per unit area and per unit volume for pantiliners, diapers and adult incontinence garments can be calculated based on the differences in caliper, noted hereinabove.

Preferably, the denier and strength of the capillary channel fibers will be chosen such that the batt of fibers herein will have a ratio of wet:dry caliper of at least about 80%, more preferably at least about 90%. This ensures that the batt will retain its soft and form-fitting qualities even in use.

(4). Use of Capillary Channel Fiber Batts in Absorbent Articles

The capillary channel fiber batts will have some amount of holding capacity for fluids, such as menstrual fluids. Accordingly, the capillary channel fiber batts can, if desired, comprise the entire absorbent core of, for example, pantiliners. However, for most uses, the capillary channel fiber batts will be used in conjunction with an absorbent core, and the core will serve as a reservoir for fluids which are transferred from the capillary channel fiber batt into the core. Such cores may comprise an air-laid felt of cellulosic fibers, or mixtures of cellulosic fibers with absorbent gelling materials.

Due to the extremely fine structure of the cellulosic fibers in such absorbent cores, the cores exhibit high suctional forces which tend to draw away fluids from the capillary channel fibers 25 and into the core 24 for ultimate storage. This is precisely the intended effect. Thus, for a sanitary napkin, typical cores which comprise from about 1 g to about 5 g of multiple cellulosic fibers and, optionally, from about 0.5 g to about 1.5 g of absorbent gelling material. As fluid proceeds into the article, it encounters the capillary channel fiber network, which distributes the fluid and then surrenders it to the absorbent core 24, thereby at least partially "renewing" the capillary channel fiber network for the next infusion of fluid. Thus, the capillary channel fibers draw fluid through the topsheet, thereby leaving the topsheet with a fresh, dry appearance and feel, then surrender the fluid to the underlying absorbent core, and are thus able to continue the process until the core is saturated.

(5). Contact Between the Topsheet and the Capillary Channel Fibers

The bun 26 of capillary channel fibers is kept in close contact with the overlying topsheet 22. This can be achieved by a number of suitable mechanics. These include but are not limited to bonding the bun 26 to the topsheet 22 by adhesives, ultrasonics, and the like or by tensional forces. The contact between the topsheet 22 and the capillary channel fibers 25 may be so close that portions of the capillary channel fibers extend into the orifices of the topsheet.

Thus, in a highly preferred mode there is an interconnecting network between topsheet, thence into the capillary channel fiber bun, and thence into the underlying absorbent core, whereby fluid efficiently proceeds through the topsheet 22, along and through the capillary channel fibers 25 of the bun 26 and into the absorbent core 24. This interconnection is maintained even in the face of in-use stresses such as moisture, mechanical shear, and pressure-relaxation associated with physical movements of the wearer.

If an adhesive attachment is used, several factors should be kept in mind. The amounts of adhesive used and the pattern in which it is laid down should minimize the sticking of the absorbed article to the user's body.

It will also be appreciated that using excessive amounts of adhesive could undesirably clog capillary channels in the fibers, thereby diminishing their effectiveness. Accordingly, "noninterfering" amounts of the adhesive are used. Such amounts can vary, depending on the adhesive chosen, the pattern in which it is laid down, the width of the capillary channels in the fibers, and the like. Controlling the area of adhesive and the diameter of the adhesive lines in the spiral in the manner illustrated also serves to minimize the sticking of the articles to the user's body.

The adhesive should be non-irritating to the skin and otherwise toxicologically-acceptable for use in close contact with delicate body tissues. The adhesive should maintain its bonding properties when moisture is not present, i.e., when the article is being manufactured, and, most preferably, when moisture is present, i.e., when the article is being used.

The adhesive should bond both to the material used to manufacture the topsheet and to the material used to manufacture the capillary channel fibers. If the topsheet or the fibers are surface-treated, e.g., in a hydrophilization process, the nature of the surface treatment will have to be considered when selecting the adhesive.

Typical adhesives useful herein include materials selected from latex adhesives and hot melt adhesives.

Figure 9:
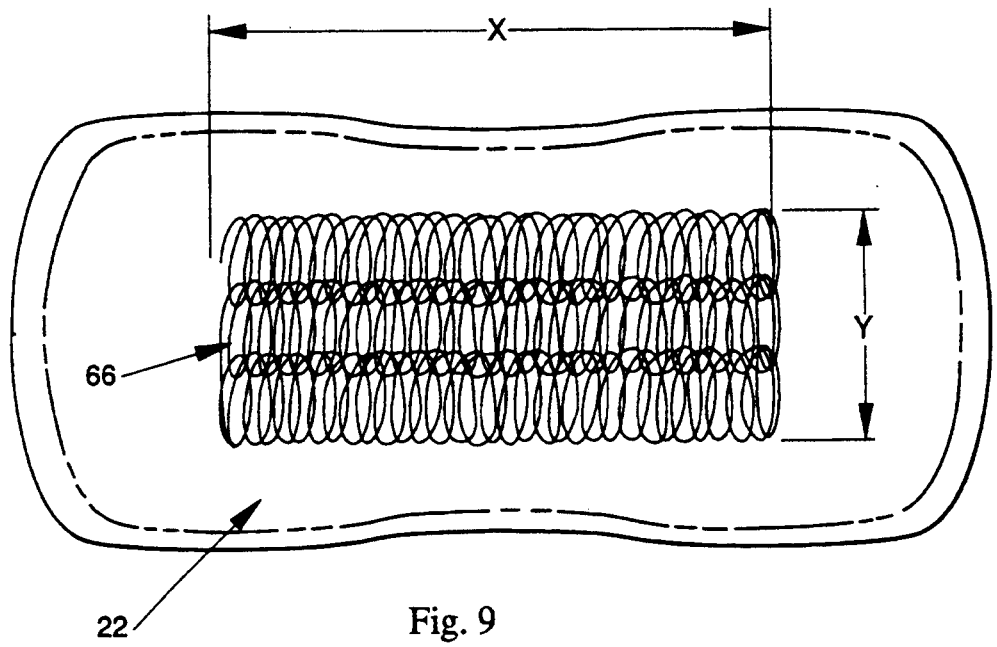
FIG. 9 shows the underside of a topsheet and one preferred multispiral pattern of glue lines used to affix the topsheet to the layer of capillary channel fibers.
Figure 10:
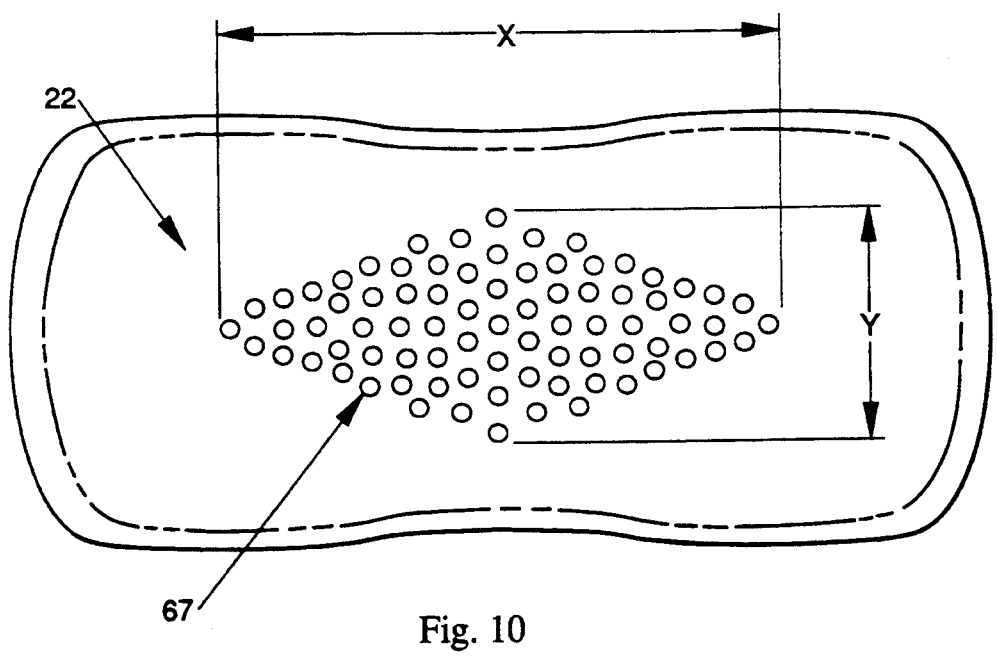
FIG. 10 shows the underside of a porous topsheet and another preferred pattern of adhesive spots used to affix the topsheet to the layer of capillary channel fibers.

The adhesive can be laid down in a random pattern, however, it is most preferred that a spiral, or multiple spiral, pattern, such as the one illustrated in FIG. 9, be used. The lines of adhesive 66 are applied to the underside or garment side of the topsheet 22 in a spiral pattern using a 0.2 mm nozzle, but application using nozzles at least as large as 0.6 mm is satisfactory. Alternatively, the spot pattern of FIG. 10 can be used to apply the adhesive 67 to the topsheet 22, but is less preferred.

Suitable adhesives are available from Findley Adhesives, Inc., especially hot melt adhesive 4031, and latex 8085. The type of adhesive can vary somewhat depending on the type of finish present on the capillary channel fibers. Suitable finishes include Eastman's LK 5483, LK 5563 and most preferably Eastman's LK 5570, as well as the polymer available as MILEASE T, which is well-known in the detergency arts (see, for example, U.S. Pat. No. 4,132,680) as a fiber-coating ethylene terephthalate/polyethyleneglycol terephthalate soil release polymer, and which is available from ICI Americas.

The amounts of adhesive employed will vary, but typically range from about 0.05 g for a 2 in. × 5 in. spiral pattern to about 0.07 g for a 2 in. × 7 in. spiral pattern, using a hot melt adhesive. For a latex adhesive, from about 0.1 g to about 0.15 g for a 2 in. × 5 in. pattern will suffice. For the spot pattern, about 0.05 g is used in an area of ca. 2 in. × 5 in.

The adhesives may be applied in an open pattern network of filaments of adhesives as it disclosed in U.S. Pat. No. 4,573,986 issued to Minetola et al. on Mar. 4, 1986. Some suitable attachment means that utilized an open pattern network filaments comprising several lines of adhesive filaments is rolled into a spiral pattern are illustrated by the apparatus and methods disclosed in U.S. Pat. 3,911,173 issued to Sprague, Jr. on Oct. 7, 1975; U.S. Pat. No. 4,785,996 issued to Zieker et al. on Nov. 22, 1978; and U.S. Pat. No. 4,842,666 issued to Werenicz on Jun. 27, 1989.

Close contact between the topsheet and the underlying layer of capillary channel fibers can be further improved by applying pressure during the gluing process and/or by "combing" the uppermost capillary channel fibers in the layer to provide individual fiber protrusions which give better contact with the adhesive.

(6). Contact Between the Capillary Channel Fibers and the Absorbent Core

It is preferable that there also be close contact between the capillary channel fibers 25 and the absorbent core 24 in order to efficiently transfer liquids to the absorbent core 24.

This close contact can also be achieved in a number of ways. These include, but are not limited to, the use of adhesives, ultrasonic bonds, by tensional forces, by providing a roughened surface of the absorbent core, or by needle-punching, or otherwise inserting some of the capillary channel fibers into the absorbent core.

Preferably, as shown in FIGS. 2 and 11, the base of the tuft 26 of capillary channel fibers is slipped into a slit in the top of the core 24.

The tuft 26 of capillary channel fibers has two end extensions designated 94. The end extensions 94 extend outward at the base of the tuft 26 in opposite directions. The end extensions 94 preferably extend along the longitudinal centerline "1". The end extensions 94 are in fluid (i.e., liquid) transporting contact with the upper portion of the tuft 26 of capillary channel fibers. The end extensions 94 are also in fluid transporting contact with the absorbent core 24 laminate.

The bun 26 of capillary channel fibers 25 provides the sanitary napkin 20 with a component having liquid transportation capabilities. The capillary channel fibers 25 will typically be primarily used to transport liquids deposited on the bun 26 due to the capillary gradient described above, rather than to absorb the same. The bun 26 of capillary channel fibers may, therefore, also be referred to as a transport layer. This transport layer has several key features.

The transport layer 21 or more preferably the bun 26 comprises an upper portion 45 that extends above the main absorbent component of the sanitary napkin, the absorbent core 24. This upper portion 45 of the bun 26 can be positioned in close contact with the wearer's body. Even more advantageously, the upper portion 45 of the bun 26 can be of such a size and shape and resiliency that it can fit at least partially within the space between the wearer's labia. This allows it to more readily intercept exudates that leave the wearer's body.

The end extensions 94 of the bun 26 provide a liquid transportation component with conduits for transporting liquids directly to the absorbent core 24. Even more preferably, the end extensions 94 are capable of transporting liquids to the interior of the absorbent core 24. This provides the sanitary napkin 20 with another advantage.

Generally, when exudates are simply deposited on top of an absorbent component, such as the absorbent core 24, they can be absorbed readily along the top surface of the absorbent component. However, liquids tend to remain in and fill the upper parts of the core first. This blocks the transportation of exudates to the lower regions of the core. The end extensions 94 reduce the potential for this problem to occur. The end extensions 94 eliminate the need for liquids to travel through one part of an absorbent storage component to get to the place where available absorbent capacity exists. The construction of the sanitary napkin 20 described above is only one possible arrangement of the transport component, however. Many other suitable arrangements of components are possible if the principles discussed above are followed. For instance, the end extensions 94 (or other portions of the capillary channel fiber bun) could be placed in contact with the absorbent core 24 in a number of different ways. The following is a non-limiting list of possible relationships between the end extensions 94 and the absorbent core 24. They are generally arranged from more to less preferred. The end extensions could be: (1) surrounded by the other components of the absorbent core; (2) commingled or integrated into the other components; (3) placed between two or more layers of the other components, such as described immediately above; (4) placed under at least one other layer; or, (5) placed on top of the other components.

The sanitary napkin 20 may have other types of transport components or layer(s) positioned between the topsheet and the absorbent core. Preferably, the embodiment shown in FIGS. 2 and 11 has an additional acquisition layer (or "secondary topsheet") 27 positioned between the topsheet 22 and the absorbent core 24. Such an additional acquisition layer could be used to distribute body exudates that are deposited longitudinally or laterally outside of the bun 26 of capillary channel fibers to the absorbent core 24. These other types of transport components, the methods of securing the same in absorbent articles, and the functions served by the same are described in U.S. Pat. Nos. 4,950,264 and 5,009,653 issued to Osborn, and in U.S. patent application Ser. No. 07/810,774, "Absorbent Article Having Fused Layers", filed Dec. 17, 1991 in the names of Cree et al (now abandoned). The transport component or components may be comprised of other types of material (instead of capillary channel fibers). These include, but are not limited to nonwoven or woven webs of synthetic fibers including polyester, polypropylene, or polyethylene; natural fibers including cotton or cellulose; blends of such fibers; or any equivalent materials or combinations of material.

E. Optional Retaining Means

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive provides a means for securing the sanitary napkin in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the national Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 39 in order to keep the adhesive 36 from drying out or adhering to a surface other than the crotch portion of the panty prior to use. Suitable release liners 39 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner 39 and thereafter placing the sanitary napkin 20 in a panty so that the adhesive 36 contacts the panty. The adhesive 36 maintains the sanitary napkin in its position within the panty during use.

F. Optional Features

The sanitary napkin 20 may also be provided with two flaps 34, each of which are adjacent to and extend laterally from the side edge of the absorbent core. The flaps 34 are configured to drape over the edges of the wearer's panties in the crotch region so that the flaps 34 are disposed between the edges of the wearer's panties and the thighs. The flaps 34 serve as least two purposes. First, the flaps 34 help serve to prevent soiling of the wearer's body and panties by menstrual fluid, preferably by forming a double wall barrier along the edges of the panties. Second, the flaps 34 are preferably provided with attachment means on their garment surface so that the flaps 34 can be folded back under the panty and attached to the garment facing side of the panty. In this way, the flaps 34 serve to keep the sanitary napkin 20 properly positioned in the panty.

The flaps 34 can be constructed of various materials including materials similar to the topsheet, backsheet, tissue, or combinations of these materials. Further, the flaps 34 may be a separate element attached to the main body portion of the napkin or can comprise extensions of the topsheet 22 and the backsheet 23 ( i.e., unitary).

A number of sanitary napkins having flaps suitable or adaptable for use with the sanitary napkins of the present invention are disclosed in U.S. Pat. No. 4,687,478 entitled "Shaped Sanitary Napkin with Flaps", issued to Van Tilburg on Aug. 18, 1987; U.S. Pat. No. 4,589,876 entitled "Sanitary Napkin", issued to Van Tilburg on May 20, 1986; and U.S. Pat. No. 4,608,047, entitled "Sanitary Napkin Attachment Means", issued to Medingly on Aug. 26, 1986.

G. Assembly of the Components of a Sanitary Napkin

The preferred sanitary napkin embodiment shown in FIG. 1 has its components assembled with several different types of attachment mechanisms. These attachment mechanisms (or attachment means) will be discussed with reference to FIG. 11. For the purposes of this discussion the absorbent core 24 will comprise the cross-linked cellulosic laminate described above. The absorbent core 24, as noted above, is preferably sandwiched between the nonwoven secondary topsheet 27 and a nonwoven layer 28 to form a "core/nonwoven sheet sandwich 51. The components of the core/nonwoven sheet sandwich 51 can be secured together in any suitable manner. The components in the embodiment shown in FIG. 1 are secured together by stitching lines 48. The stitching of these components serves several purposes. These include, but are not limited to the following. The stitching holds the components of the core/nonwoven sheet sandwich 51 together. Stitching is a preferred mechanism for holding these components together because it is a very permanent method of bonding such components together. The stitching also holds up well in the presence of liquids.

The stitching also enhances the transfer of liquids between the layers of the core/nonwoven sheet sandwich. The stitching secures the components of the core/nonwoven sheet sandwich together in such a manner that the components are held and sustained in close contact with each other. As discussed above, this contact relationship is one of the features needed for transportation of liquids down into the underlying components.

The stitching need not be limited to the core/nonwoven sheet sandwich, however. Stitching can be used to secure together any of the components the sanitary napkin located between (and including) the topsheet 22 and the backsheet 23. The topsheet 22 is bonded to the tuft of capillary channel fibers by a topsheet bonding adhesive 66. The backsheet 23 is bonded to the garment side of the core/nonwoven laminate 51. This is accomplished in the embodiment shown in FIG. 11 by two strips of construction adhesive 52.

The topsheet 22 and the backsheet 23 are then secured together. The topsheet 22 and the backsheet 23 have a length and dimension and width dimensions that are greater than those of the absorbent core 24. The topsheet 22 and backsheet 23, therefore, extend beyond the edges of the absorbent core 24 to form at least a part of the periphery 30 of the sanitary napkin.

The topsheet 22 and backsheet 23 are secured to each other or at least a part of the periphery 30 of the sanitary napkin 20 by a perimeter heat seal. The formation of this perimeter heat seal is described in greater detail below which describes methods of making a sanitary napkin 20 of the present invention.

The description of the mechanisms for securing the various components of the sanitary napkin 20 is but one method of constructing the sanitary napkin. Any of the components of the sanitary napkin 20 can be secured together by adhesives, stitching, heat and/or pressure bonds, dynamic mechanical bonds, ultrasonic bonds, intramingling or entanglement of the fibers or other structural elements comprising the components of the sanitary napkin, such as by melt blowing the fibers comprising one component onto another component, or by another means known in the art.

While particular embodiments of the present invention have been illustrated and described, it would be obvious to those skilled in the art that various other changes and modifications can be made without departing from the spirit and scope of the invention. It is therefore intended to cover in the appended claims all such changes and modification that are within the scope of this invention.

H. Method for Making the Sanitary Napkin

The sanitary napkin 20 is assembled in the following manner. For simplicity, the assemblies are described in terms of one possible method. The steps described below can be carried out in many other orders. There are also numerous other ways to assemble the sanitary napkin. All such alternatives are within the scope of the present invention.

The components for the absorbent core 24 are obtained. The absorbent core 24 used in the preferred laminate described above comprises two layers of cross-linked cellulose fibers 41 and 42 with absorbent gelling particles 40 therebetween. The absorbent gelling material particles 40 are placed on top of the web (or portion thereof) that will form the bottom layer 42 of cross-linked cellulosic fibers. The batt of capillary channel fibers 25 is placed on top of the absorbent gelling material 40. The capillary channel fibers 25 are oriented so that the extensions 94 will extend along the longitudinal centerline 1 of the completely assembled sanitary napkin.

The web of cross-linked cellulosic fibers (or portion therein) that will form the upper layer 41 of the core 24 is provided with a longitudinal slit. The slit is provided in the portion of the upper layer 41 that will lie in the central region of the completely assembled sanitary napkin.

The upper layer 41 of the core 24 is placed on top of the capillary channel fibers 25 and layered particles of absorbent gelling material 40. The upper portion 45 of capillary channel fibers 25 is pulled up through the slit to form a tuft 26. This leaves the upper portion 45 of the bun 26 exposed. The extensions 94 remain in place within the absorbent core laminate on top of the layer of absorbent gelling material 40. This forms an absorbent core pre-assembly.

The secondary topsheet 27 material 15 provided. The layer of material comprising the secondary topsheet 27 is also provided with a longitudinal slit. The secondary topsheet 27 is placed on the body facing side of the absorbent core pre-assembly. The upper portion 45 of the tuft 26 of capillary channel fibers 25 is pulled through the slit in a secondary topsheet 27. A nonwoven layer 28 is positioned on the garment-facing side of the core pre-assembly. This forms the absorbent core/nonwoven sheet laminate 51. The components of the absorbent core/nonwoven sheet laminate 51 are then secured together by stitching or adhesive. An adhesive is placed on the backsheet 23 to secure the absorbent core to the backsheet material. The backsheet 23 is then placed on the garment-facing side of the absorbent core pre-assembly. The topsheet 22 is then sprayed with the topsheet bonding adhesive 66 on its garment-facing side. Preferably, the adhesive 66 is applied in a spiral pattern such as that shown in FIG. 9.

The topsheet 22 is then placed on top of the absorbent core/nonwoven sheet laminate 51 (with the tuft 26 still protruding from the core/nonwoven sheet laminate 51). This forms a pre-assembled sanitary napkin. The pre-assembled sanitary napkin is then ready to be sealed. The longitudinal side margins and end margins are then sealed. In the preferred process described herein, the longitudinal side margins and the end margins of the sanitary napkin 20 are sealed by a heated element. The heated element is essentially used to "iron" the longitudinal side margins and the end margins together.

3. Alternative Embodiments of the Sanitary. Napkin of the Present Invention

A. Multiple Tufts of Capillary Channel Fibers

Figure 12:
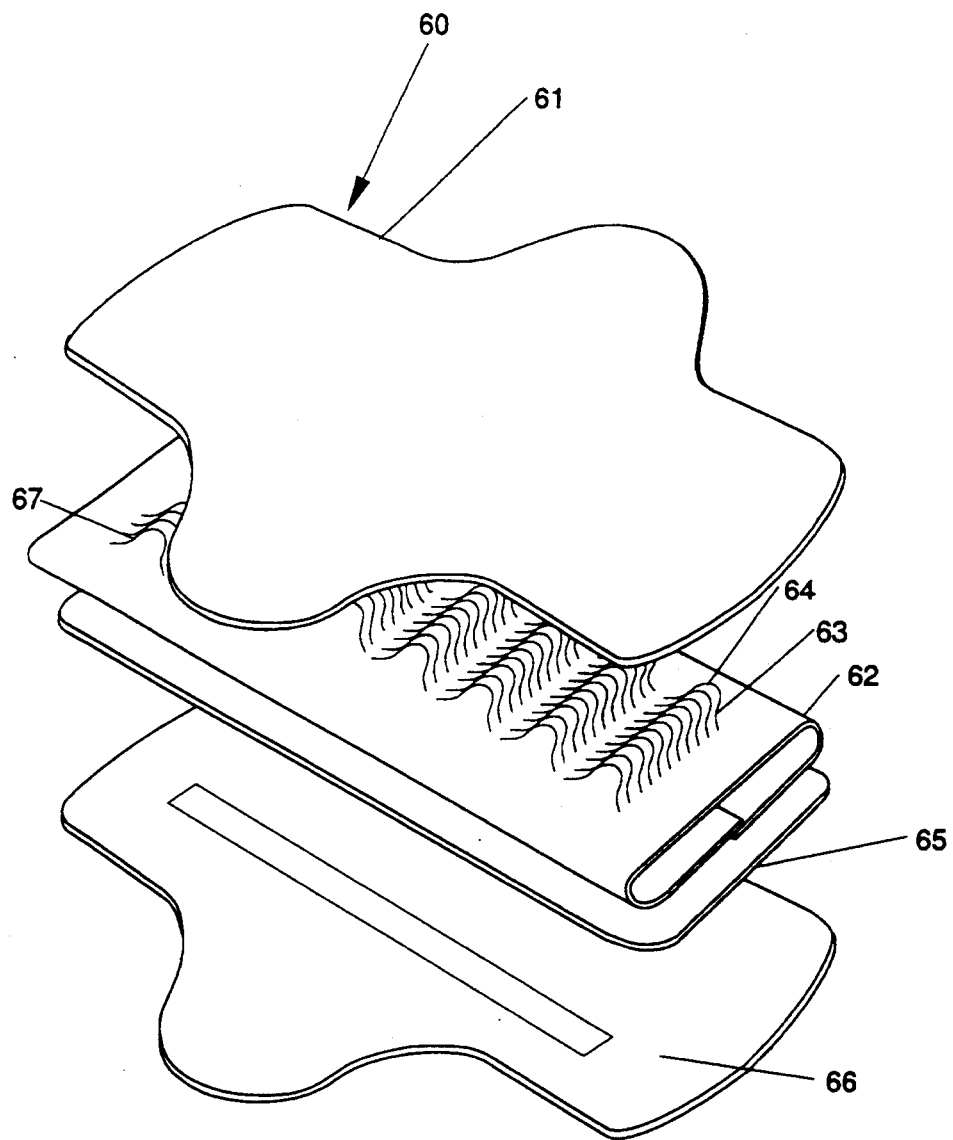
FIG. 12 shows an exploded perspective view of another embodiment of the sanitary napkin of the present invention.

FIG. 12 is an alternative embodiment of a sanitary napkin 60 of the present invention. The sanitary napkin 60 preferably comprises a liquid-pervious topsheet 61, a liquid-impervious backsheet 66 joined to the topsheet 61, and an absorbent core 62 positioned between the topsheet 61 and the backsheet 66. The sanitary napkin 60 also includes a nonwoven layer 65 positioned between the absorbent core 62 and the backsheet 66. The nonwoven layer 65 serves to keep the material of the core 62 from tearing when the core (comprised of cross-linked cellulose fibers) and the layers of the sanitary napkin are stitched.

Sanitary napkin 60 preferably includes a transport layer consisting of a plurality of tufts 64 of capillary channel fibers 63. In this embodiment the capillary channel fibers 63 are sewn or stitched into the absorbent core 62 providing the tufted configuration 64 as shown. The number, size and shape of the tufts 64 can be varied accordingly by the maker to provide the desired resilience, comfort and fit for the sanitary napkin 60. The tufts 64 are preferably oriented substantially in the z-direction. The upper portion 67 of the tufts 64 extend above the uppermost surface of the core 62. The lower portion of the tufts 64 extend below the uppermost surface of the core 62. In an alternative configuration, the upper portion of the tufts 64 are cut, thus eliminating the looped portion of the tuft 64.

Fluid deposited on the topsheet 61 is then passed in the z-direction through the tufts 64 of capillary channel fibers 63 toward the ultimate storage layer or absorbent core 62. This creates a standoff from the topsheet 61 as the fluid (e.g., menses and/or urine) is removed from the skin of the wearer.

B. Multiple Tufted Pad Having a Hole in the Topsheet

Figure 13:
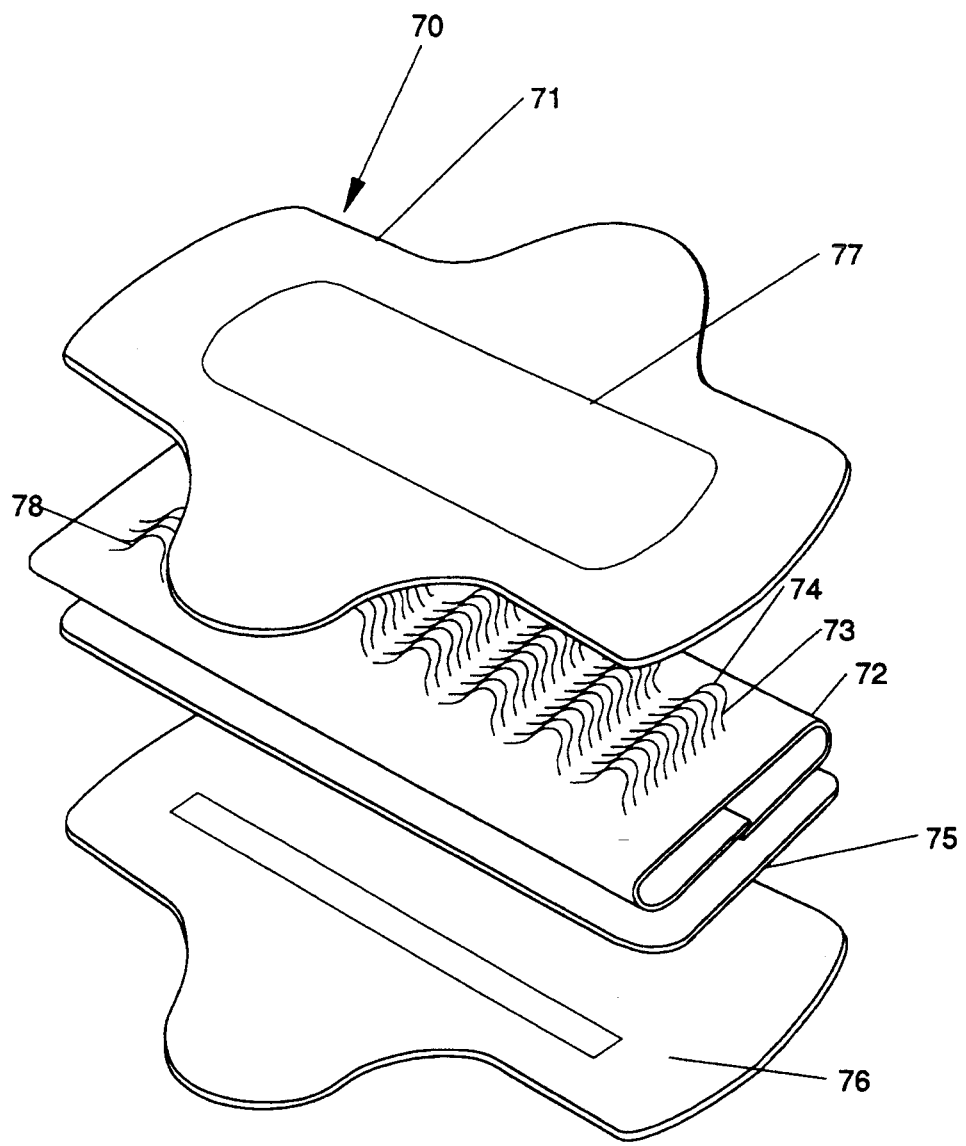
FIG. 13 shows an exploded perspective view of another embodiment of the sanitary napkin of the present invention.

In the alternative embodiment shown in FIG. 13, the overall arrangement and positioning of the respective layers is very similar to that of FIG. 12. The sanitary napkin in FIG. 13 comprises a liquid-pervious topsheet 71, a liquid impervious backsheet 76 joined to the topsheet 71, and an absorbent core 72 positioned between the topsheet 71 and backsheet 76. The sanitary napkin 70 also includes a nonwoven layer 75 positioned between the absorbent core 72 and the backsheet 76. The sanitary napkin 70 also includes a plurality of tufts 74 of capillary channel fibers 73 which are sewn into the absorbent core 72. The tufts 74 are preferably oriented substantially in the z-direction. The upper portion 78 of the tufts 74 extend above the uppermost surface of the core 72. The lower portion of the tufts 74 extend below the uppermost surface of the core 72.

In addition, the topsheet 71 is provided with an aperture 77. When the various components of the sanitary napkin 70 are placed together the plurality of tufts 74 of capillary channel fibers 73 will extend through the aperture 77 in the topsheet 71. Therefore, the capillary channel fibers 73 will be in direct fluid contact with the skin of the user. In the arrangement of FIG. 13, it is preferable to have capillary channel fibers 73 having a "C"-shaped cross-section with stabilizing legs depending therefrom as illustration in FIG. 4. The capillary channel fibers having a "C"-shaped cross-section have been found to be more gentle and non-irritating to the user's skin. By providing direct contact between the capillary channel fibers and the user's body, bodily fluid deposited on the absorbent article 70 does not have to penetrate the topsheet 71 before contacting the capillary channel fibers 73. This will provide quicker transportation of the bodily fluids away from the user's body and into the absorbent core 72.

C. Single Bun Pad

Figure 14:
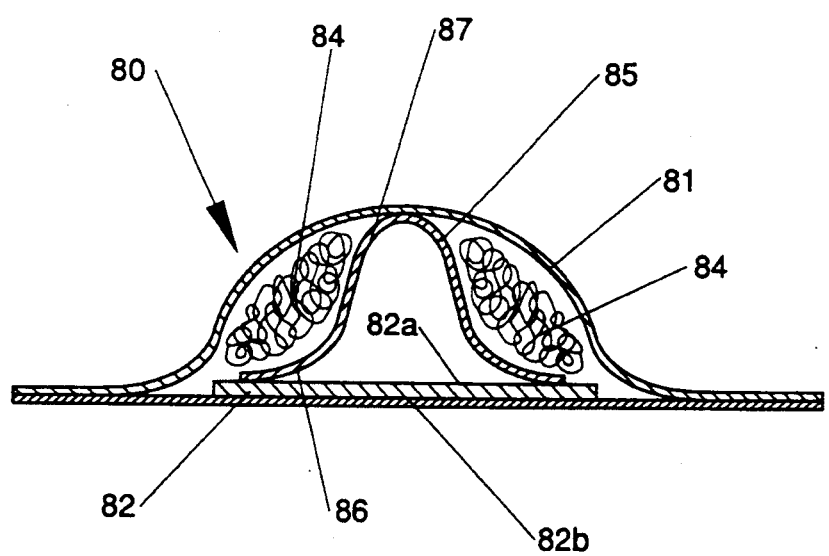
FIG. 14 shows an cross-sectional view of another embodiment of the sanitary napkin of the present invention.

FIG. 14 is a cross-sectional view of an alternative embodiment of a sanitary napkin 80 of the present invention. Sanitary napkin 80 preferably comprises a liquid-pervious topsheet 81, a liquid-impervious backsheet 86 joined to the topsheet 81, and a primary absorbent core 82 positioned between the topsheet 81 and the backsheet 86. The primary absorbent core 82 has a first surface 82a facing the body of the user and a second surface 82b aligned opposite the first surface 82a. The sanitary napkin 80 also includes a transport layer 85 positioned between the topsheet 81 and the primary absorbent core 82. The transport layer 85 has a lower portion 86 and an upper portion 87. Preferably, the transport layer 85 is positioned on or above the first or body-facing surface 82a of the primary absorbent core 82. The upper portion 82 of the transport layer 85 is oriented substantially in the z-direction toward the topsheet 81. The lower portion 86 of the transport layer 85 extends substantially in the longitudinal direction.

Sanitary napkin 80 preferably includes a secondary absorbent structure 84. In this embodiment the secondary absorbent structure 84 preferably comprises a nonwoven low density material, a foam, or any loosely arranged fibers. Preferably the secondary absorbent 84 is a high loft material having a density less than that of the transport layer 85. The secondary absorbent structure 84 substantially surrounds the transport layer 85. In the embodiment shown in FIG. 14 the primary absorbent core 82 will preferably have a density greater than that of the transport layer 85. In this configuration fluid deposited on topsheet 81 is then passed in a z-direction through either the secondary absorbent structure 84 or through the transport layer 85 toward the primary or ultimate storage layer or absorbent core 82.

In addition to providing standoff from the topsheet 81 the transport layer 85 and secondary absorbent 84 act as a resilient body, providing a better overall fit for the user. In addition, the transport layer 85 and the secondary absorbent 84 preferably have a lower density than that of absorbent core 82 allowing for fluid transfer in the z-direction toward the ultimate or primary storage core 82.

While particular embodiment of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal direction, a transverse direction, and a z-direction, said absorbent article comprising:
   (a) a liquid pervious topsheet;
   (b) a liquid impervious backsheet;
   (c) an absorbent core positioned between said topsheet and said backsheet, said core having an uppermost surface facing said topsheet and a lowermost surface facing said backsheet, said uppermost surface of said core having an aperture therein; and
   (d) a transport layer having a lower portion and an upper portion, the lower portion of said transport layer being positioned below the uppermost surface of said core and being oriented substantially in the longitudinal direction of said absorbent article, the upper portion of said transport layer being gathered into a bun, said bun extending through said aperture in said uppermost surface of said absorbent core toward said topsheet.

2. The absorbent article according to claim 1 wherein said transport layer comprises capillary channel fibers having external capillary channels.

3. An absorbent article according to claim 2 wherein the capillary channel fibers are hydrophilic.

4. An absorbent article according to claim 3 wherein the capillary channel fibers have a "C"-shaped cross-section.

5. The absorbent article according to claim 4 wherein the capillary channel fibers are substantially curled and a portion of the fibers partially protrude into said topsheet.

6. The absorbent article according to claim 1 wherein said absorbent core comprises absorbent gelling material disposed between the uppermost and lowermost surfaces of said core.

7. The absorbent article according to claim 1 wherein said absorbent core comprises capillary channel fibers having external capillary channels.

8. The absorbent article according to claim 1 further comprising a secondary topsheet superposed on the uppermost surface of said core.

9. The absorbent article according to claim 1 wherein said topsheet comprises an aperture permitting said transport layer to extend through said aperture in said topsheet.

* * * * *

UNITED STATES PATENT AND TRADEMARK OFFICE
CERTIFICATE OF CORRECTION

PATENT NO. : 5,382,245
DATED : January 17, 1995
INVENTOR(S) : Thompson, et al.

It is certified that error appears in the above-indentified patent and that said Letters Patent is hereby corrected as shown below:

On the Title page, item [57] Abstract, "In-use" should read --In use--.

In Col. 1, line 8, "now abandoned" should read --(now abandoned)--.

In Col. 4, line 61, "cut-away" should read --cut away--.

In Col. 5, line 10, "non-woven" should read --nonwoven--.

In Col. 5, line 62, "intra-fiber" should read --interfiber--.

In Col. 6, line 12, "inter-fiber" should read --interfiber--.

In Col. 6, line 12, "interfiber" should read --intra-fiber--.

In Col. 6, line 16, "inter-fiber" should read --interfiber--.

In Col. 6, line 23, "inter-fiber" should read --interfiber--.

In Col. 6, line 55, "non-absorbent" should read --nonabsorbent--.

In Col. 7, line 18, "abandoned" should read --(now abandoned)--.

In Col. 9, line 23, "channel s" should read --channels--.

In Col. 9, line 33, "pending" should read --(pending)--.

In Col. 11, line 8, "inter-fiber" should read --interfiber--.

In Col. 11, line 15, "inter-fiber" should read --interfiber--.

In Col. 12, lines 49 and 50, "now abandoned" should read --(now abandoned)--.

In Col. 16, line 46, "The" should begin the start of a new paragraph.

In Col. 16, line 54, "The" should begin the start of a new paragraph.

In Col. 17, line 6, "These" should begin the start of a new paragraph.

In Col. 17, line 13, "The" should begin the start of a new paragraph.

In Col. 17, line 63, "The" should begin the start of a new paragraph.

UNITED STATES PATENT AND TRADEMARK OFFICE
CERTIFICATE OF CORRECTION

PATENT NO. : 5,382,245
DATED     : January 17, 1995
INVENTOR(S) : Thompson, et al.

It is certified that error appears in the above-indentified patent and that said Letters Patent is hereby corrected as shown below:

In Col. 20, line 66, "liquid impervious" should read --liquid-impervious--.

Signed and Sealed this

Twenty-fourth Day of December, 1996

Attest:

BRUCE LEHMAN

Attesting Officer     Commissioner of Patents and Trademarks